United States Patent [19]

Slack et al.

[11] Patent Number: 5,319,054

[45] Date of Patent: Jun. 7, 1994

[54] LIQUID METHYLENE DIPHENYL DIISOCYANATE

[75] Inventors: William E. Slack, Moundsville; Hersel T. Kemp, II, New Martinsville, both of W. Va.

[73] Assignee: Miles Inc., Pittsburgh, Pa.

[21] Appl. No.: 116,096

[22] Filed: Sep. 2, 1993

[51] Int. Cl.$^5$ ............................................. C08G 18/72
[52] U.S. Cl. .................................... 528/48; 528/45; 528/49; 528/55; 528/67; 252/182.22; 560/27
[58] Field of Search ................ 528/48, 45, 49, 55, 528/67; 252/182.22; 560/27

[56] References Cited

U.S. PATENT DOCUMENTS

| | | | |
|---|---|---|---|
| 3,644,457 | 2/1972 | Köniq et al. | 260/453 S P |
| 4,055,548 | 10/1977 | Carleton et al. | 260/77.5 AT |
| 4,115,429 | 9/1978 | Reiff et al. | 260/453 SP |
| 4,118,411 | 10/1978 | Reiff et al. | 260/453 SP |
| 4,160,080 | 7/1979 | Köenig et al. | 528/59 |
| 4,261,852 | 4/1981 | Carroll et al. | 528/59 |
| 4,490,300 | 12/1984 | Allen et al. | 260/453 SP |
| 4,738,991 | 4/1988 | Narayan | 521/124 |
| 4,866,103 | 9/1989 | Cassidy et al. | 521/159 |
| 4,910,333 | 3/1990 | Slack | 560/351 |

FOREIGN PATENT DOCUMENTS 46-99176 12/1971 Japan .

*Primary Examiner*—Maurice J. Welsh
*Attorney, Agent, or Firm*—Joseph C. Gil; Godfried R. Akorli

[57] ABSTRACT

The present invention relates to a process for the production of a allophanate-modified MDI which is a storage stable liquid at 25° C. comprising (A) reacting (i) one equivalent of a diisocyanate and (ii) one equivalent of an aliphatic alcohol containing from 1 to about 36 carbon atoms or aromatic alcohol containing from 6 to 18 carbon atoms to form a diurethane of the diisocyanate, (B) reacting the product of (A) with 4,4'-diphenylmethane diisocyanate containing from 2 to 60% by weight 2,4'-MDI and less than 6% by weight of the 2,2'-MDI, in an amount sufficient to provide an allophanate having an isocyanate group content of about 12.0 to 30.0%.

6 Claims, No Drawings

LIQUID METHYLENE DIPHENYL DIISOCYANATE

BACKGROUND OF THE INVENTION

1. Field of the Invention

The present invention relates to liquid methylene diphenyl diisocyanates (MDI). More specifically, the present invention relates to liquid allophanate-modified MDI prepolymers and the methods of making and using the same.

2. Brief Description of the Prior Art

Liquid methylene diphenyl diisocyanates are generally known in the art. U.S. Pat. No. 3,644,457 discloses room temperature, stable, liquid isocyanates derived from one mole of diphenylmethane diisocyanate and 0.1 to 0.3 mols of poly-1,2-propylene ether glycol.

U.S. Pat. No. 4,055,548 discloses liquid isocyanate prepolymer compositions obtained by reacting polymethylene polyphenylisocyanate containing from about 65 to 85 percent by weight of methylene bis(phenylisocyanate with a polyoxyethylene glycol having molecular weight of from 200 to 600 in an equivalent ratio 0.0185–0.15:1.

U.S. Pat. Nos. 4,115,429 and 4,118,411 disclose low temperature (as low as −5 degrees Centigrade), storage stable liquid diphenylmethane diisocyanates which are produced by reacting diphenylmethane diisocyanates having a specified 2,4-isomer content with propylene glycol or poly-1,2-propylene ether glycol.

U.S. Pat. No. 4,261,852 discloses liquid polyisocyanate compositions comprising (a) the reaction product of 90 to 50% by weight of a reaction product of diphenylmethane diisocyanate and a polyoxypropylene diol or triol having hydroxyl equivalent weight of from 750 to 3000, said reaction product having NCO content of from 8 to 26% by weight, and (B) from about 10 to 50% by weight of a diphenylmethane diisocyanate containing from 30 to 65% by weight of diphenylmethane diisocyanate, the remainder being polymethylene polyphenyl polyisocyanate.

U.S. Pat. No. 4,490,300 discloses room temperature stable liquid isocyanates which are derived by reacting diphenylmethane diisocyanate with an aliphatic diol having a pendant aromatic group, e.g., 2-methyl-2-phenyl-1,3-propanediol or phenyl-1-2-ethanediol.

U.S. Pat. No. 4,490,300 discloses room temperature stable liquid isocyanates which are derived by reacting diphenylmethane diisocyanate with monoallylether of trimethylolpropane.

U.S. Pat. No. 4,738,991 discloses organic polyisocyanates characterized by allophanate linkages which are prepared by reacting an organic polyisocyanate including 2,4- and 4,4-methylenediphenyl diisocyanate with poly- or monohydric alcohol in the presence of an organo metallic catalyst. The catalyst is then deactivated using a compound such as an inorganic acid, organic acid, organic chloroformate or an organic acid chloride.

U.S. Pat. No. 4,866,103 discloses a polyisocyanate composition for use in producing elastomers in a RIM process, said composition being the product of reacting an alcohol and/or thiol having an average functionality of from about 1.5 to about 4 and an average equivalent weight of at least 500 with at least 2 equivalents per hydroxyl and/or thiol equivalent of an organic polyisocyanate including 4,4- and 2,4-isomers of diphenylmethane diisocyanate under such conditions that at least about 20% of the initially formed urethane and/or thiourethane groups are converted to allophanate and/or thioallophanate groups.

Other prior art relating to the preparation of allophanates which contain isocyanates are British Patent 994,890 which relates to the reaction of urethane isocyanates with excess diisocyanate either by heat alone or in the presence of a catalyst such as a metal carboxylate, a metal chelate or a tertiary amine, until the isocyanate content is reduced to that which is obtained theoretically when the complete reaction of the urethane groups is achieved.

U.S. Pat. No. 4,160,080 discloses a process for producing allophanate containing aliphatically and/or cycloaliphatically bound isocyanate groups in which compounds containing urethane groups are reacted with polyisocyanates having aliphatic and/or cycloaliphatic isocyanate groups in the presence of a strong acid. The process is generally conducted at a temperature of from 90° C. to 140° C. for about 4 to 20 hours.

Japanese Patent Application No. 1971-99176 discloses a method of preparing liquid diphenylmethane diisocyanate by reacting diphenylmethane diisocyanate with aliphatic monovalent alcohol.

By the present invention there is provided a novel liquid isocyanate.

SUMMARY OF THE INVENTION

In accordance with the foregoing, the present invention, in the first embodiment encompasses a process for the production of a prepolymer containing an allophanate-modified MDI which is a storage stable liquid at 25° C. comprising (A) reacting (i) one equivalent of a diisocyanate selected from the group consisting of hexamethylene diisocyanate (HDI), isophorone diisocyanate (IPDI), toluene diisocyanate (TDI), diphenylmethylene diisocyanate (MDI), and hydrogenated MDI with (ii) one equivalent of an aliphatic alcohol containing 1 to about 36 carbon atoms or aromatic alcohol containing 6 to 18 carbon atoms to form a diurethane of the diisocyanate, B) reacting the product of (A) with a specified isomer composition of diphenylmethane diisocyanate in an amount sufficient to provide a liquid allophanate modified MDI having an NCO content of about 12.0 to 30.0%. Typically, the diphenylmethane diisocyanate isomer composition contains 4,4'-diphenylmethane diisocyanate, from 2 to 60% by weight 2,4'-MDI and less than 6% by weight of the 2,2'-MDI.

In the second embodiment, the present invention encompasses a process as recited above, further comprising reacting the allophanate-modified MDI with (a) an organic material containing two or more hydroxy, primary amine or secondary amino groups or any combination thereof having a molecular weight of from 400 to 6000, (b) a diol having a molecular weight of from 60 to 200 or a combination of (a) and (b) wherein the resultant liquid prepolymer has an isocyanate group content of from 5 to 29% by weight.

The allophanate-modified MDI prepolymers obtained from the above processes are also encompassed by the invention.

It is a distinct feature of the invention that the resultant allophanate-modified MDI prepolymers are stable and liquid at 25° C. By the term "stable" herein is meant that the isocyanate has no more than one percent absolute change in NCO content and no more than ten percent change in the viscosity when stored at 25° C. for 3 months. By the term "liquid" herein is meant that the modified isocyanate does not precipitate solids when stored at 25° C. for 3 months.

The prepolymers are particularly useful in that automotive reaction injection molding (RIM), shoe soles and rigid foam applications.

DETAILED DESCRIPTION OF THE INVENTION

In the first embodiment, the prepolymer containing allophanate-modified MDI is characterized in that it is stable and liquid at 25° C. and has an isocyanate content of about 12 to 30% and preferably 17 to 28%. In the second embodiment, the allophanate-modified MDI is characterized in that it has an isocyanate group content of about 5 to 29% and preferably 12 to 27% by weight. The allophanate-modified MDI can be prepared by reacting a diisocyanate with an aliphatic or aromatic alcohol in order produce a diurethane, followed by reacting the diurethane with the specified MDI isomer composition to form a diallophanate. More specifically, the diurethane can be obtained by reacting one equivalent of a diisocyanate with one equivalent of an aliphatic alcohol containing 1 to about 36 carbon atoms or aromatic alcohol containing 6 to 18 carbon atoms to form a diurethane of the diisocyanate.

The diisocyanate is selected from the group consisting of hexamethylene diisocyanate (HDI), isophorone diisocyanate (IPDI) toluene diisocyanate (TDI), diphenylmethylene diisocyanate (MDI), and hydrogenated MDI.

Aliphatic alcohols useful herein are those that can react with the diphenylmethane diisocyanate to form diurethanes which can be converted to allophanates in accordance with the invention. The useful aliphatic or aromatic alcohols can contain about 1 to 36 and preferably 4 to 16 carbon atoms. Illustrative but non-limiting examples of the aliphatic alcohols can be selected from the group consisting of cycloaliphatic alcohols, aliiphatic alcohols containing aromatic groups, and aliphatic alcohols containing groups that do not react with isocyanates e.g., ether groups and halogens such as bromine and chlorine. Specific but non-limiting examples of the aliphatic alcohols can be selected from the group consisting of 1-butanol, cetyl alcohol, 2-methoxyethanol and 2-bromoethanol.

Specific examples of the aromatic alcohols can be selected from the group consisting of phenol, m-cresol and 1-naphthol.

In the reaction of the aliphatic or aromatic alcohol with the diisocyanate, the NCO to OH equivalent is about 1:1 with the reaction being monitored till an NCO value of 0 to 0.5 is attained. Solvents which are typically inert to the isocyanate, for example toluene, tetrahydrofuran, o-dichlorobenzene or the like can be employed.

In accordance with the invention, the process comprises reacting the resulting diurethane with the specified isomer composition of diphenylmethane diisocyanate in an amount sufficient to provide an allophanate having an isocyanate group content of about 12.0 to 30.0%. As set forth above, the isomer composition of the diphenylmethane diisocyanate comprises about 2 to 60% and preferably 2 to 30% by weight 2,4'-diphenylmethane diisocyanate and less than 6% and preferably about 0 to 1.0% by weight of the 2,2'-diphenylmethane diisocyanate, and the rest being 4,4'-diphenylmethane diisocyanate.

The allophanate-forming reaction is usually conducted in the presence of a catalyst. The useful catalysts are those which can be neutralized or otherwise stopped from adversely catalyzing subsequent reactions. Illustratively, a catalyst such as zinc acetylacetonate can be employed, and a catalyst stopper such as acidic materials, e.g., anhydrous hydrochloric acid, sulfuric acid, benzoyl chloride, Lewis acids and the like in the ratio of 2 equivalents of the acid to each mole of the zinc acetylacetonate. Other allophanate catalysts such as zinc 2-ethylhexanoate, cobalt 2-ethylhexanoate, cobalt naphthanate, lead linoresinate or the like can be employed.

In a preferred embodiment of the process of the invention, the allophanate can be prepared by reacting the diisocyanate, as described above, with an aliphatic or aromatic alcohol, at about 20° C. to about 115° C. The resultant diurethane is dissolved in the specified MDI isomer composition and converted to an allophanate modified MDI at 90°-110° C., using zinc acetylacetonate as catalyst, and benzoyl chloride as a stopper for the catalyst in a 2:1 weight ratio of benzoyl chloride to zinc acetylacetonate.

In the second embodiment of the invention, the process further to the afore-described process steps comprises reacting the allophanate modified MDI such as described above with a high and/or a low molecular weight organic material containing two or more and preferably 2 to 3 active hydrogen groups such as hydroxyl, primary or secondary amino groups or the like. The high molecular weight organic material can have a molecular weight from 400 to 6000 and preferably 2000 to 5000. The low molecular weight range can be from 60 to 200 and preferably 76 to 90.

The subject urethane, urea, or bioret reaction is carried out in a manner which is well known by, say, heating the reactants to a temperature from about 40° to 150° C. and preferably from 50° to 100° C. to form urethane or urea and heating to a temperature of 100° to 150° C. and preferably 110° to 120° C. to form the biuret.

The useful organic materials containing two or more hydroxyl groups having a molecular weight of 400 to 6000 can be a polyol selected from the group consisting of polyester polyols, polyether polyols, polyhydroxy polycarbonates, polyhydroxy polyacetals, polyhydroxy polyacrylates, polyhydroxy polyester amides and polyhydroxy polythioethers. The polyester polyols, polyether polyols and polyhydroxy polycarbonates are preferred.

Suitable polyester polyols include reaction products of polyhydric, preferably dihydric alcohols to which trihydric alcohols may be added and polybasic, preferably dibasic carboxylic acids. Instead of these polycarboxylic acids, the corresponding carboxylic acid anhydrides or polycarboxylic acid esters of lower alcohols or mixtures thereof may be used for preparing the polyesters. The polycarboxylic acids may be aliphatic, cycloaliphatic, aromatic and/or heterocyclic and they may be substituted, e.g. by halogen atoms, and/or unsaturated. The following are mentioned as examples: succinic acid; adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride; tetrachlorophthalic acid anhydride, endomethylene tetrahydrophthalic acid anhydride; glutaric acid anhydride; maleic acid; maleic acid anhydride; fumaric acid; dimeric and trimeric fatty acids such as oleic acid, which may be mixed with monomeric fatty acids; dimethyl terephthalates and bis-glycol terephthalate. Suitable polyhydric alcohols include, e.g. ethylene glycol; propylene glycol-(1,2) and -(1,3); butylene glycol-(1,4) and -(1,3); hexanediol-(1,6); octanediol-(1,8); neopentyl glycol; cyclohexanedimethanol (1,4-bis-hydroxymethylcyclohexane); 2-methyl-1,3-propanediol; 2,2,4-trimethyl-1,3-pentanediol; triethylene glycol; tetraethylene glycol; polyethylene glycol; dipropylene glycol; polypropylene glycol; dibutylene glycol and polybutylene glycol, glycerine and trimethlyolpropane. The polyesters may also contain a portion of carboxyl end groups. Polyesters of lactones, e.g. ε-caprolactone or hydroxyl carboxylic acids, e.g. ω-hydroxycaproic acid, may also be used.

Polycarbonates containing hydroxyl groups include those known per se such as the products obtained from the reaction of diols such as propanediol-(1,3), butanediol-(1,4) and/or hexanediol-(1,6), diethylene glycol, triethylene glycol or tetraethylene glycol with phosgene, diarylcarbonates such as diphenylcarbonate or with cyclic carbonates such as ethylene or propylene carbonate. Also suitable are polyester carbonates obtained from the above-mentioned polyesters or polylactones with phosgene, diaryl carbonates or cyclic carbonates.

Suitable polyether polyols are obtained in known manner by the reaction of starting compounds which contain reactive hydrogen atoms with alkylene oxides such as ethylene oxide, propylene oxide, butylene oxide, styrene oxide, tetrahydrofuran, epichlorohydrin or mixtures of these alkylene oxides. It is preferred that the polyethers do not contain more than about 10% by weight of ethylene oxide units. Most preferably, polyethers obtained without the addition of ethylene oxide are used. Suitable starting compounds containing reactive hydrogen atoms include the polyhydric alcohols set forth for preparing the polyester polyols and, in addition, water, methanol, ethanol, 1,2,6-hexane triol, 1,2,4-butane triol, trimethylol ethane, pentaerythritol, mannitol, sorbitol, methyl glycoside, sucrose, phenol, isononyl phenol, resorcinol, hydroquinone, 1,1,1- or 1,1,2-tris(hydroxylphenyl)-ethane.

Polyethers modified by vinyl polymers are also suitable for the process according to the invention. Products of this kind may be obtained by polymerizing, e.g. styrene and acrylonitrile in the presence of polyethers (U.S. Patent Nos. 3,383,351; 3,304,273; 3,523,095; 3,110,695 and German Patent No. 1,152,536).

Among the polythioethers which should be particularly mentioned are the condensation products obtained from thiodiglycol on its own and/or with other glycols, dicarboxylic acids, formaldehyde, aminocarboxylic acids or amino alcohols. The products obtained are either polythis-mixed ethers, polythioether esters or polythioether ester amides, depending on the co-components.

Amine-terminated polyether useful herein can be prepared by reacting a primary amine with a polyether containing terminal leaving groups such as halides, or mesylates as disclosed in commonly assigned U.S. patent application Ser. No. 07/957,929, filed on Oct. 7, 1992, or as disclosed in U.S. Patent Nos. 3,666,726, 3,691,112 and 5,066,824.

Suitable polyacetals include the compounds which can be prepared from aldehydes, e.g. formaldehyde, and glycols such as diethylene glycol, triethylene glycol, ethoxylated 4,4'-dihydroxy-diphenyldimethylmethane, and hexanediol-(1,6). Polyacetals suitable for the purpose of the invention may also be prepared by the polymerization of cyclic acetals.

Suitable polyhydroxy polyester amides and polyamines include the predominantly linear condensates obtained from polybasic saturated and unsaturated carboxylic acids or their anhydrides and polyvalent saturated or unsaturated aminoalcohols, diamines, polyamines and mixtures thereof.

Suitable monomers for producing hydroxy-functional polyacrylates include acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate and 2-isocyanatoethyl methacrylate.

The low molecular weight material preferably containing two hydroxyl groups having an average molecular weight of 60 to 200 may be used in combination with or instead of the high molecular weight material containing two or more hydroxyl groups. The useful low molecular weight materials include the polyhydric alcohols which have previously been described for the preparation of the polyester polyols and polyether polyols. Dihydric alcohols are preferred. The weight ratio of the low molecular weight to the high molecular weight material containing two or more hydroxyl groups can be from 0.001 to 2 and preferably 0.01 to 0.40.

In addition to the above-mentioned components which are preferably difunctional, monofunctional and even small portions of trifunctional and higher functional components generally known in polyurethane chemistry, such as trimethylolpropane, may be used in special cases in which slight branching of the resultant product is desired.

In the process of the invention, the hydroxyl functional material(s) can be reacted with the allophanate over the temperature range of 40° to 150° and preferably 50° to 100° C., over a period of time sufficient to complete the reaction. Catalysts and solvents can be employed to aid the reaction. Examples of the useful catalysts to promote the urethane reactions can be selected from the group consisting of di-n-butyltin dichloride, di-n-butyltin diacetate, di-n-butyltin dilaurate, triethylenediamine, bismuth nitrate and the like.

Examples of the useful solvents can be selected from the group consisting of toluene, tetrahydrofuran, and chlorobenzene.

The resultant product of the first embodiment is a liquid isocyanate prepolymer having an isocyanate group content of 12 to 30 percent and preferably 17 to 28 percent. The resultant product of the second embodiment is a liquid isocyanate prepolymer having an isocyanate group content of 5 to 29% and preferably 12 to 27%. These liquid isocyanate prepolymers have been found to be particularly useful in the preparation of isocyanate reaction products such as polyurethanes.

The invention is further illustrated but is not intended to be limited by the following examples in which all parts and percentages are by weight unless otherwise specified.

EXAMPLES

MDI-X: Djphenylmethane diisocyanate which contains less than 6% by weight 2,2'-MDI and in which X represents the percent by weight 2,4'-MDI with the remainder being the 4,4'- and 2,2'-MDI.

EXAMPLE 1

7.1 parts of MDI-20 and 5.0 parts of 2-pentanol were charged to a stirred reactor and heated at 80° C. for about 2 hours. 92.9 parts of MDI-20 is then added to the reactor. 0.1 part of zinc acetylacetonate is then added to the reaction mixture which is then heated to 110° C. and held for 2 hours. 0.3 part of benzoyl chloride is then added and the reaction mixture is cooled to about 25° C. to afford a clear liquid having an NCO content of 27.1% and a viscosity at 250° C. of 100 mpa.s.

EXAMPLES 2-8

The same procedure and conditions as described in Example 1. In the first step, equal equivalents of MDI and the alcohol are first reacted followed by addition of the remainder MDI. Any changes from Example 1 are set forth in the following table along with the % NCO and viscosity of the resulting clear liquid modified isocyanate.

TABLE 1

| Example | MDI-X/pbw | Alcohol/pbw | Time (min.) | % NCO | Visc. @ 25° C. mPa·s |
|---|---|---|---|---|---|
| 2 | 55/100 | methanol/2.3 | 157 | 27.0 | 330 |
| 3 | 20/100 | 1-propanol/3.7 | 78 | 27.4 | 182 |
| 4 | 30/100 | 1-propanol/3.7 | 85 | 27.4 | 110 |
| 5 | 40/100 | 1-propanol/3.7 | 65 | 27.4 | 101 |
| 6 | 30/100 | 1-pentanol/5.0 | 90 | 27.4 | 130 |
| 7 | 20/100 | 1-pentanol/5.0 | 73 | 27.4 | 105 |
| 8 | 40/100 | 1-pentanol/5.0 | 40 | 27.4 | 84 |

EXAMPLE 9

10 parts 2,4-toluene-diisocyanate (TDI) and 14.9 parts 2-octanol were charged to a stirred flask, 0.005 parts dibutyltin dilaurate catalyst was added and heated to 80° C. for about 1 hour 30 min. To the diurethane is added 112.7 parts MDI-2 and 0.01 parts zinc acetylacetonate, which is then heated to 90° C. and held for about 60 min. 0.03 part benzoyl chloride is then added at 90° C. and the reaction mixture is cooled to about 25° C. to afford a clear liquid, having an NCO content of 24.0% and a viscosity at 25° C. of 1700 mpa.s.

EXAMPLES 10 THROUGH 21

Used the same procedure and conditions as described in Example 9. In the first step equal equivalents of the alcohol and the diisocyanate, for example hexamethylene diisocyanate (HDI), MDI-2 or TDI, are first reacted followed by addition of MDI-2. Any changes from Example 9 are set forth in the following table along with the % NCO and viscosity.

TABLE 2

| Example | Diisocyanate (pbw) | Alcohol (pbw) | MDI-2 (pbw) | % NCO | Visc @ 25° C. mPa·s |
|---|---|---|---|---|---|
| 10 | TDI/10 | 1-butanol/8.5 | 111.5 | 25.3 | 1300 |
| 11 | TDI/10 | 2-butanol/8.5 | 115.0 | 25.3 | 1700 |
| 12 | TDI/10 | 1-decylalcohol/18.2 | 120.8 | 23.9 | 1100 |
| 13 | TDI/10 | 1-pentanol/10.1 | 100.6 | 24.1 | 2200 |
| 14 | TDI/10 | 2-pentanol/10.1 | 100.6 | 24.1 | 2500 |
| 15 | HDI/10 | 2-octanol/16.1 | 119.2 | 23.9 | 1200 |
| 16 | HDI/10 | 2-pentanol/10.9 | 106.2 | 23.9 | 2150 |
| 17 | HDI/10 | 2-butanol/9.2 | 101.9 | 23.9 | 3300 |
| 18 | MDI/10 | 1-decylalcohol/12.7 | 91.7 | 24.1 | 1700 |
| 19 | MDI/10 | 2-octanol/10.4 | 86.0 | 24.1 | 2200 |
| 20 | MDI/10 | 2-pentanol/7.0 | 77.6 | 23.1 | 3900 |
| 21 | MDI/10 | 2-butanol/5.9 | 74.8 | 23.9 | 4010 |

Although the invention has been described in detail in the foregoing for the purpose of illustration, it is to be understood that such detail is solely for that purpose and that variations constituting other embodiments can be made therein by those skilled in the art without departing from the spirit and scope of the invention except as it may be limited by the claims.

What is claimed is:

1. A process for the production of a allophanate-modified MDI which is a storage stable liquid at 25° C. comprising (A) reacting (i) one equivalent of a diisocyanate and ii) one equivalent of an aliphatic alcohol containing 1 to about 36 carbon atoms or aromatic alcohol containing 6 to 18 carbon atoms to form a diurethane of the diisocyanate, B) reacting the product of (A) with 4,4'-diphenylmethane diisocyanate containing from 2 to 60% by weight 2,4'-MDI and less than 6% by weight of the 2,2'-MDI, in an amount sufficient to provide an allophanate having an isocyanate group content of about 12.0 to 30.0%.

2. The process of claim 1 wherein the allophanate is prepared at 90°-110° C. in the presence of a zinc acetylacetonate catalyst.

3. The process of claim 2 wherein benzoyl chloride is used as the stopper for the catalyst.

4. The process of claim 1 further comprising reacting the allophanate-modified MDI with (a) an organic material containing two or more hydroxy, primary amine or secondary amino groups or any combination having a molecular weight of from 400 to 6000 (b) a diol having a molecular weight of from 60 to 200 or a combination of (a) and (b) to produce a liquid prepolymer having an isocyanate group content of from 5 to 29% by weight.

5. An allophanate-modified MDI which is stable and liquid at 25° C. and has an isocyanate content of about 12 to 30.0% which is prepared by the process of claim 1.

6. An allophanate-modified MDI which is stable and liquid at 25° C. and has an isocyanate content of about 5 to 29% which is prepared by the process of claim 4.

* * * * *